(12) United States Patent
Fleischmann

(10) Patent No.: US 6,398,767 B1
(45) Date of Patent: Jun. 4, 2002

(54) PROCESS AND DEVICE FOR APPLICATION OF ACTIVE SUBSTANCES TO A WOUND SURFACE AREA

(76) Inventor: Wilhelm Fleischmann, Wieselweg 26, D-74321 Bietigheim-Bissingen (DE)

( * ) Notice: Subject to any disclaimer, the term of this patent is extended or adjusted under 35 U.S.C. 154(b) by 0 days.

(21) Appl. No.: 09/085,484

(22) Filed: May 27, 1998

(30) Foreign Application Priority Data

May 27, 1997 (DE) .......................................... 197 22 075

(51) Int. Cl.⁷ ........................... A61M 1/00; A61F 13/00
(52) U.S. Cl. ...................... 604/313; 604/304; 604/305
(58) Field of Search ................................ 604/289, 290, 604/305, 306, 307, 308, 313, 315, 316; 600/573, 575; 424/447, 448, 449

(56) References Cited

U.S. PATENT DOCUMENTS

| | | | | |
|---|---|---|---|---|
| 4,382,441 A | * | 5/1983 | Svedman | 604/291 |
| 4,953,565 A | * | 9/1990 | Tachibana et al. | 604/290 |
| 5,139,023 A | * | 8/1992 | Stanley et al. | 128/637 |
| 5,176,663 A | * | 1/1993 | Svedman et al. | 604/305 |
| 5,291,887 A | * | 3/1994 | Stanley et al. | 128/637 |
| 5,782,871 A | * | 7/1998 | Fujiwara et al. | 604/313 |

FOREIGN PATENT DOCUMENTS

| | | | |
|---|---|---|---|
| DE | 29 53 373 A1 | 1/1981 | |
| DE | 33 27 586 A1 | 2/1984 | |
| DE | 34 41 893 C2 | 5/1988 | |
| DE | 37 13 420 A1 | 11/1988 | |
| DE | 40 12 232 A1 | 10/1991 | |
| DE | 41 11 122 A | 4/1993 | ............ A61N/1/36 |
| DE | 195 17 699 A1 | 11/1996 | |
| GB | 1 549 756 A | 8/1979 | .......... A61M/27/00 |
| WO | WO 94 20041 A1 | 9/1994 | ............ A61B/19/00 |
| WO | WO 96/05873 A1 | 1/1996 | |

* cited by examiner

*Primary Examiner*—Kim M. Lewis
(74) *Attorney, Agent, or Firm*—Pendorf & Cutliff

(57) ABSTRACT

For application of active substances to a wound surface a porous padding (12) is provided upon the wound (10), which is sealingly covered over with a foil (14). A fluid active substance is introduced into the padding (12) via a supply line (22) and is then suctioned out of the padding (12) via a removal line (26). Closure mechanisms (32, 34) control the introduction of the active substance and the suctioning off of the active substance in the manner, that the active substance after being introduced remains for a predetermined dwell time in the padding (12), before it is suctioned off. After the suctioning off the vacuum in the padding (12) is maintained for a certain time period, before renewed introduction of the active substance. The opening of the closure mechanisms (32, 34) are temporally controlled to occur slowly.

8 Claims, 6 Drawing Sheets

FIG 4  a)   b)   c)
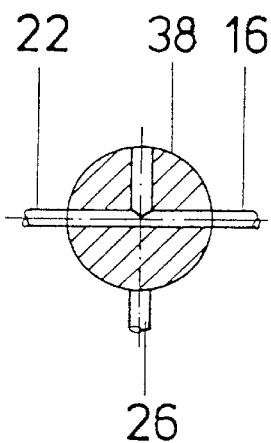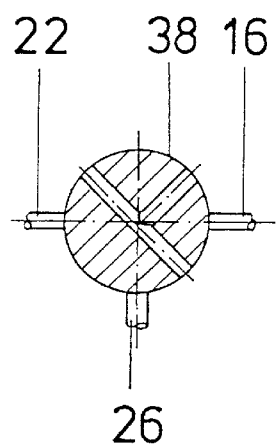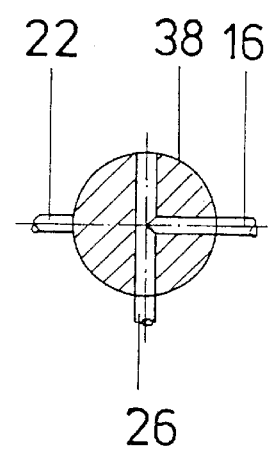
FIG 5  a)   b)   c)
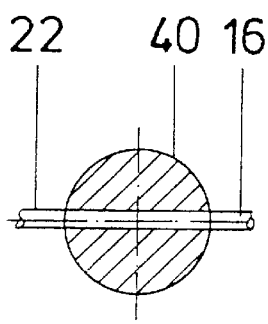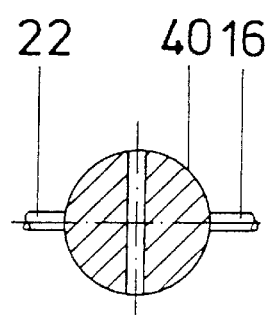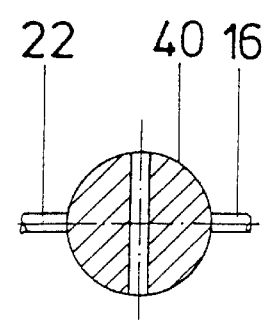
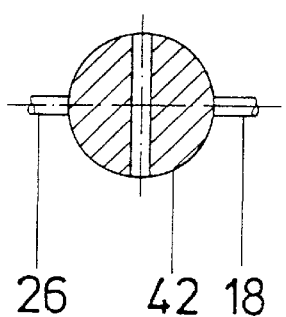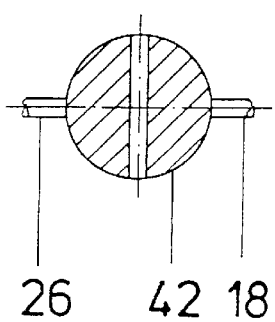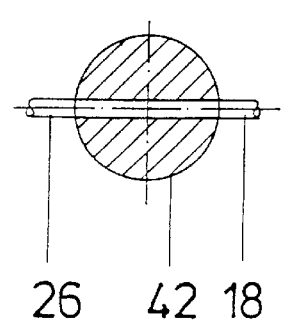

FIG 6 a) 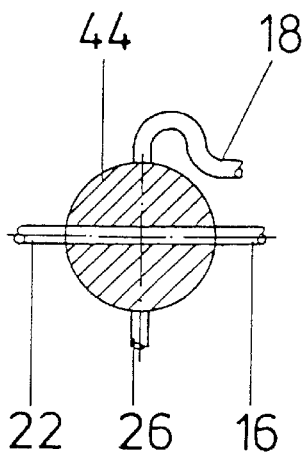 b) 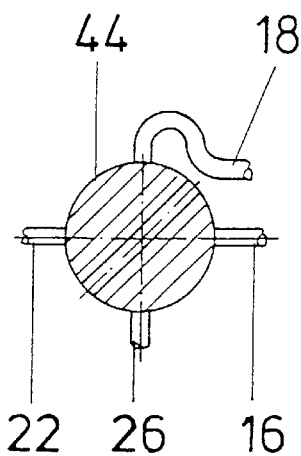 c) 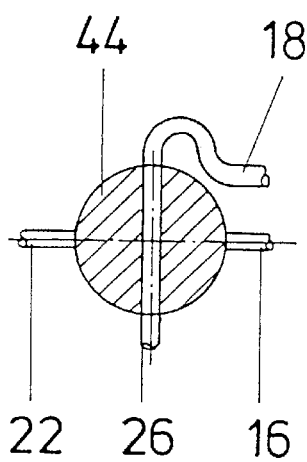
FIG 7
a) 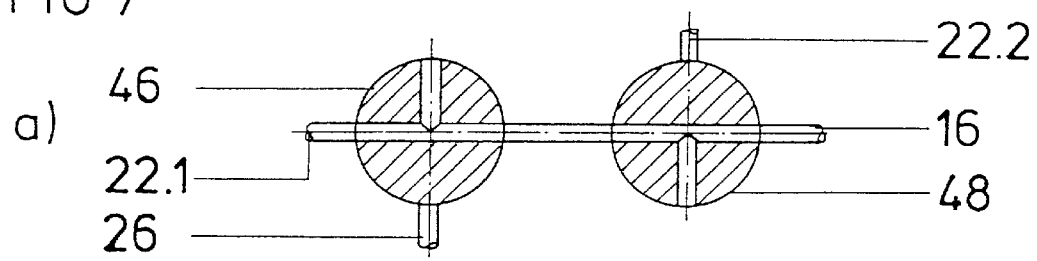
b) 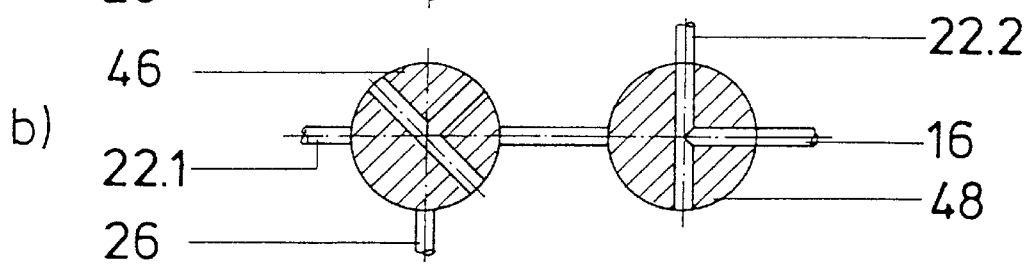
c) 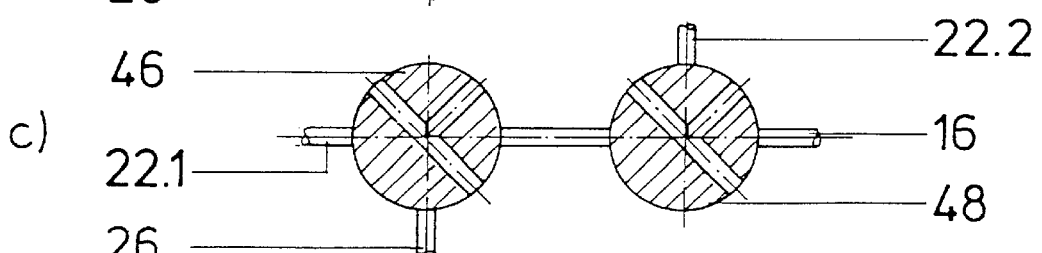
d) 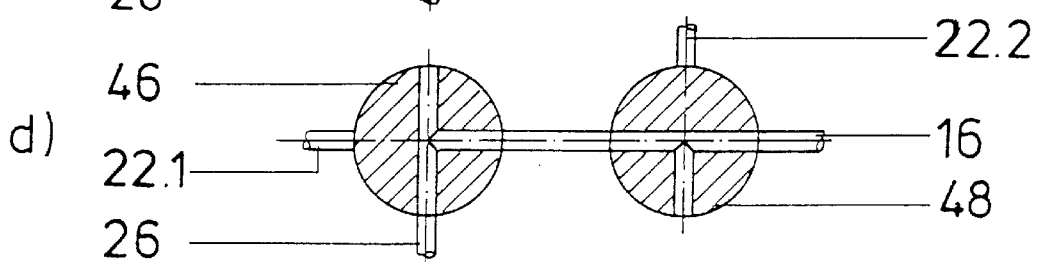

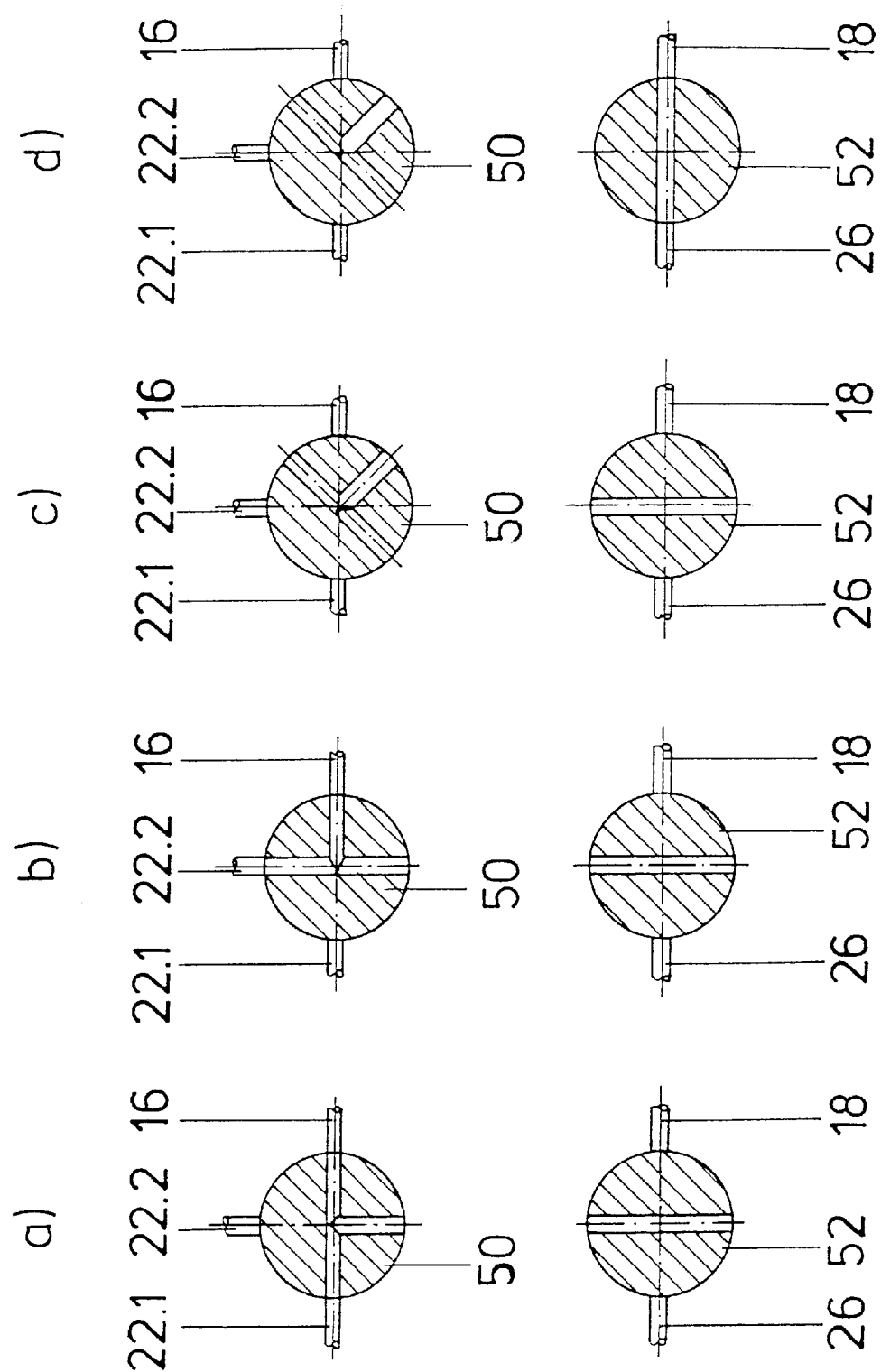

PROCESS AND DEVICE FOR APPLICATION OF ACTIVE SUBSTANCES TO A WOUND SURFACE AREA

BACKGROUND OF THE INVENTION

1. Field of the Invention

The invention concerns a process and a device for application of Claim 6.

2. Description of the Related Art

For the medicinal local treatment of wounds there have until now been employed salves, solutions or solid medicament carriers, such as resorbable collagen, antibiotic soaked bone cement or impregnated wound coverings. In particular in deep wounds there exists the difficulty, that salves are not employable, and solutions are soaked up by bandage materials and frequently do not come into sufficient contact with the inner wound surface, in order that its therapeutic effect unfolds. In the implantation of foreign body medicinal carriers, such as bone cement or resorbable materials, there occurs a loss of effectiveness by dissipation or dilution with wound secretion. Besides this, only a few medicines are available, which exhibit a local sustained effect over a long period of time. In the tissue, under certain conditions, a damaging or injurious reaction to the foreign body can result. Decomposable medicine carriers can, in their decomposition, lead to undesirable side effects.

From DE 40 12 232 A1 there is disclosed a Redon-bandage or, as the case may be, installation-bandage for the treatment of superficial and deep problematic wounds, in particular with infections, in which the wound is covered by a thin semipermeable foil. A supply line and a removal line are provided under the foil in the wound area. Active substances can be applied to the wound surface under the foil via the supply line by means of a syringe. After the desired application period the active substances can, in certain cases together with the wound secretion, be suctioned out via the removal line by means of a vacuum source. The supply line is provided with a self-acting closing safety valve, which is opened by the introduced syringe for introduction of the fluid active substances. Likewise there is provided on the removal line a closure or blockage mechanism, which closes off the output side during the application period of the active substance.

In this known installation bandage the active substances are applied directly upon the wound surface and suctioned off from the wound surface. The active substance can thus only be applied in imprecise doses and in particular in the case of large wound surface areas an even effect upon the entire surface is difficult to achieve. A long time continuous effect can not realized.

From U.S. Pat. No. 4,382,441 it is known, for treatment of wound surfaces, to lay a padding or dressing made of a porous material upon the wound surface and to sealingly cover this. The active substance to be applied is continuously conveyed through the padding, for which a fluid supply connection and a fluid removal connection communicate with the padding. The capillary effect of the porous padding optimizes the distribution of the supplied active substance over the entirety of the surface of the padding in contact with the wound surface.

The porous padding is substantially form-stable and also the sealing cover is preferably form-stable. The fluid active substance is conveyed through the padding in a continuous stream, whereby a stream distribution results, in which the fluid active substance flows essentially along the area between the fluid supply connection and fluid removal connection, while the edge areas of the padding are barely perfused. Thus, in these edge areas the active substances are only exchanged in small amounts and, further, in the edge areas accumulations of wound secretion are only insufficiently removed. Beyond this the relatively form stable padding does not lie in all areas equally against the wound surface, so that also hereby an even application of the active substance and an even removal of the wound secretion is compromised. A continuous effect is not envisioned or intended.

SUMMARY OF THE INVENTION

The invention is concerned with the task, of providing a process and device for application of active substances to a wound surface, which guarantees a high effectiveness of the applied active substance over the entire wound surface, makes possible an optimal dosing of the active substance, and enhances the wound healing process.

This task is inventively solved by a process according to Claim 1.

The basic idea of the invention is comprised therein, to lay a padding or bandage of an elastic compressible porous material upon the wound surface and to cover the wound surface and the padding with a sealing layer or foil, which closes off the wound and the padding against the atmosphere. The supply line and the removal line are respectively provided with controllable closure devices which at the appropriate time are so controlled, that the introduction of the active substance and the suctioning off of the active substance and in certain cases the wound secretion are separated from each other in time. Between the time interval in which the closure device of the supply line is opened and the active substance is supplied, and the point in time, in which the closure device of the removal line is opened in order to suction out the active substance and the wound secretion, there is programmed or provided an treatment dwell time interval, in which both closure devices are closed and the active substance statically has an effect upon the wound surface. After the suctioning off of the active substance and the wound secretion there is, besides this, a time interval programmed in which the closure mechanism of the supply side remains closed and a vacuum is maintained in the area of the wound. For this the closure mechanism of the suctioning side can remain open, so that via the vacuum source a constant vacuum is maintained in area of the wound and the wound secretion is suctioned off. The closure mechanism of the removal side can also be closed, so that the vacuum produced initially can be maintained. It is also possible in this phase that the closure mechanism of the removal side is temporarily controlled to be open, in order that the vacuum is reestablished, in case this drops below a pre-determined value.

The dwell time interval, in which the padding is impregnated or soaked with the active substance and the active substance is applied with a continuous effect upon the wound surface, is selected corresponding to the nature of the active substance, its dosing and the indications given by the condition of the wound surface. In the vacuum time interval, in which no active substance is applied and only the wound secretion is suctioned off, the bodily immunological repair and immune processes of the tissue can proceed unhindered, so that the wound healing is optimized. Thus, active treatment phases and healing phases alternate temporally one after the another. In the treatment phase the wound system is actively engaged by means of the active substances, such as for example antibiotics or antiseptics, in order to fight or combat infections and the like. Since such active substances as a rule besides the desired main effect also have undesired side effects, the active substances are suctioned off subsequent to the active treatment phase and with them the wound secretion, which contains the decomposition products produced during the active treatment phase with their, in certain cases, toxic agents. In the subsequent vacuum time interval the body's own immunological healing process can proceed optimally, without being compromised by the undesired side effects of the active substances and the decomposition products produced during the combating of the wound infection.

Preferably the closure mechanisms of the supply line and removal line are temporally so controlled, that the introduction of the active substance begins slowly and with a minimal volumetric stream. Thereby it is prevented, that wound pain is caused or increased by a too-sudden and rapid introduction of active substance. Likewise, the opening of the closure mechanism of the removal line is temporally controlled in such a manner, that the vacuum increases only gradually. A too rapid, sudden vacuum leads likewise to substantially wound pain.

The padding provided upon the wound surface is comprised of an elastic compressible porous material, preferably a PVA-sponge (polyvinyl alcohol-sponge), wherein a flexible foil is employed for covering. If a vacuum is produced in the foil-covered wound area, then the foil lies tightly upon the wound and compresses the padding. Thereby the padding lies over its entire surface equally tightly on the wound surface. This improves the suctioning off of the wound secretion during the vacuum time interval. Should the inlet opening be opened for introduction of the active substance, then the porous padding suctions the active substance in, whereby it expands on the basis of its elastic resilience. Thereby it is achieved, that the padding evenly absorbs the active substance in the manner of a sponge. The active substance is evenly distributed over the entire surface of the padding and acts upon the entire wound surface in an even manner. This is improved thereby, that the padding in the vacuum phase lies tightly against the wound surface. The even distribution of the active substance over the entire surface is not impeded or hindered during the active treatment phase, since after the end of the introduction, during the active treatment time interval, a static condition exists, in which the introduction and removal lines are closed.

Since the wound treatment can extend over a longer period of time, for example over several days, it can occur, that in particular during a longer vacuum phase the pores of the padding slightly adhere or become glued together. Such adhesion increases the resistance against the introduction of active substance. Thereby the introduction of the active substance by gravity can be impeded. In such a case it is purposeful, at the beginning of the introduction of the active substance, to first rinse the porous padding clean. For this, at the beginning of the introduction of the active substance, first a small volume of a fluid active substance is introduced under pressure, in order to rinse through the pores of the padding and to dissolve adhered areas. The introduction under pressure can advantageously be achieved by a syringe, which is connected to the inlet. Via piston pressure of the syringe a first dose of active substance can be employed for rinsing under pressure, before the introduction of the active substance occurs by gravity. In certain cases it is also possible, that the amount of the fluid active substance necessary for the entire introduction period is supplied by means of the syringe.

BRIEF DESCRIPTION OF THE DRAWINGS

In the following the invention will be described in greater detail by reference to the illustrative embodiments shown in the figures. There are shown FIG. 1 the device for application of active substances in a first embodiment, FIG. 2 a modification of the device, FIG. 3 a time diagram of the process, and FIGS. 4 through 8 various illustrative embodiments for the closure mechanisms of the device.

DETAILED DESCRIPTION OF THE INVENTION

For treatment of a large surface area deep wound 10 a padding 12 is applied. The padding 12 is comprised of a porous elastic compressible material, preferably of an open pored PVA foam material. The padding 12 is cut or trimmed to correspond to the contour of the wound 10. The wound 10 and the padding 12 are covered over by a foil 14 and sealinginly closed off. The foil 14 is so cut, that it covers over the padding 12 and the wound 10 and extends beyond the edges of the wound. The foil 14 is sealingly secured to the skin surface about the wound circumference, for example, it is adhered. The foil 14 is flexible and is comprised of a synthetic or plastic material, which permits the diffusion of water vapor, however, provides an air-tight enclosure.

In the padding 12 there is introduced a drainage tube 16, a so-called Redon-tube, which is perforated in the end area lying in the padding 12. The not perforated area of the drainage tube 16 is covered over by the foil 14 and extends out therefrom.

Figure 1:
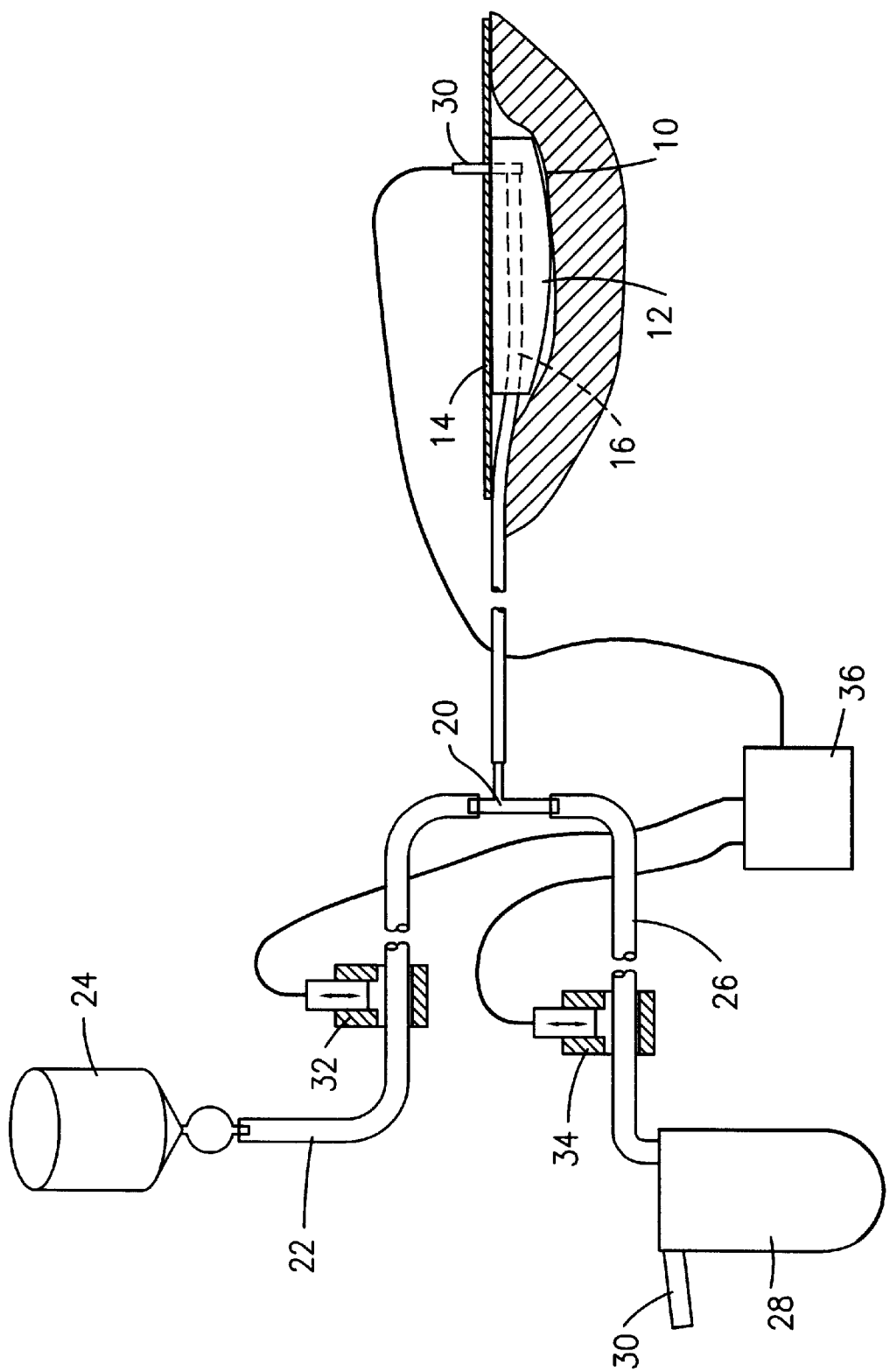

In the illustrative embodiment of FIG. 1 there is introduced in the proximal end of the drainage tube 16 a T-shaped branch or manifold piece 20. On its one connection of the manifold 20 a hose is attached as supply side 22, which leads to a known infusion container 24. On the other connection of the manifold 20 a hose is attached as removal 26 which leads to a receptacle container 28 onto which, via a connection line 30, a vacuum source is connectable. Such a receptacle container 28 is likewise known per se.

The supply line 22 has associated therewith a closure mechanism 32 and the removal line 26 has a closure mechanism 34 associated therewith. The closure mechanisms 32 and 34 are continuously adjustable between a closed position and an open position and are operated via a controller 36.

In the here shown illustrative embodiments the closure mechanisms 32 and 34 are respectively constructed as hose clamps, which include a receptacle, in which the hose of the supply line 22 or, as the case may be, the removal line 26, can be introduced. A plunger is, as indicated by arrows in the figure, controlled electromagnetically, pneumatically, hydraulically or in an otherwise known manner by the controller 36, in order that the introduced hose is pressed against a side wall and with squeezing is closed off or in order that the cross-sectional area of the hose is continuously unimpeded.

In certain cases a pressure sensor 38 can be introduced in the wound area under the foil 14, which senses the pressure existing under the foil 14 and reports this to the controller 36.

In the infusion container 24 a fluid active substance is pre-supplied, which can be introduced to the padding 12 and therewith to the wound surface via the supply line 22 and the drainage hose 16 in the case of opened closure mechanism 32 and closed closure mechanism 34. In the case of the closed closure mechanism 32 and opened closure mechanism 34 the active substance and the wound secretion produced in the wound 10 can be suctioned off via the removal line 26 into the receptacle container 28.

Figure 2:
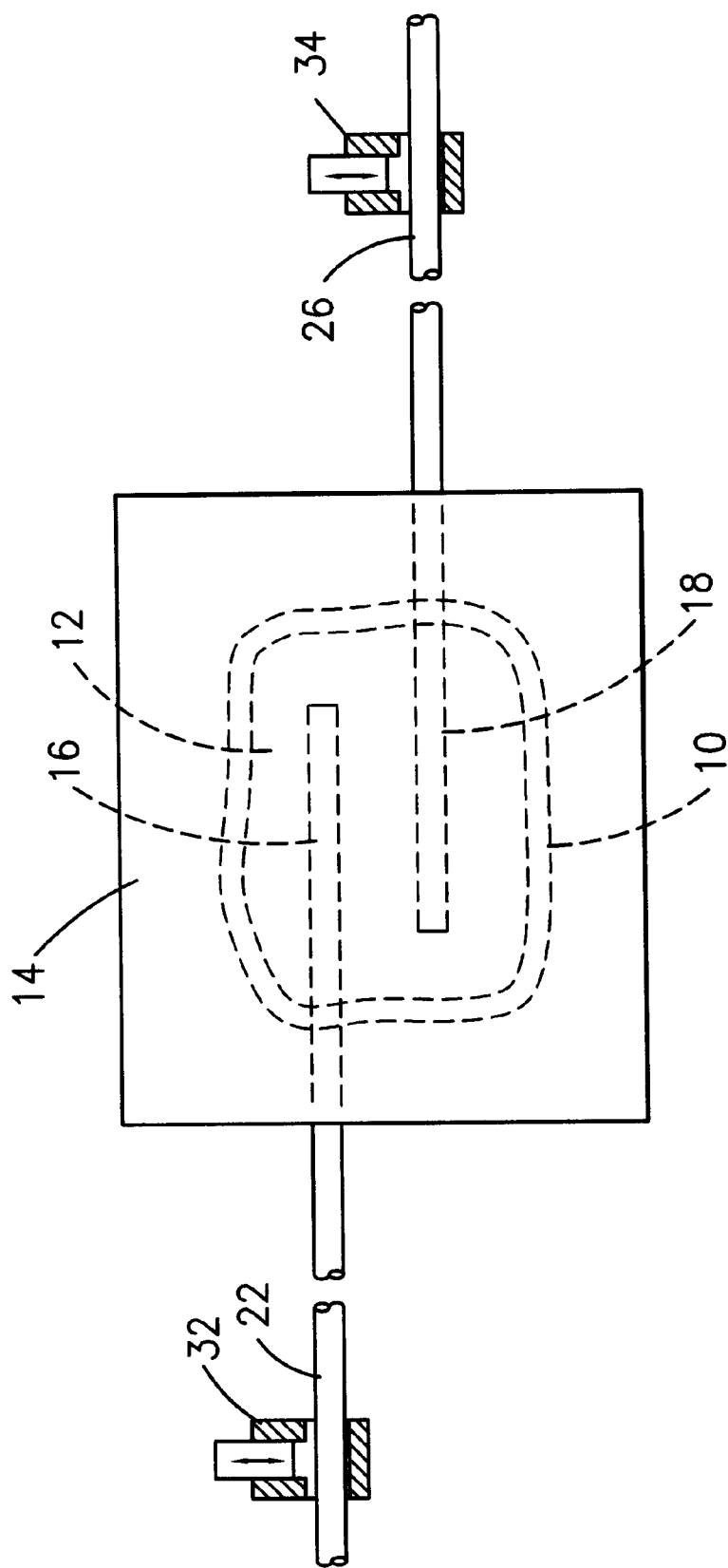

FIG. 2 shows a variation of the device, which in comparison to the illustrative embodiment of FIG. 1 differs therein, that the padding 12 introduced in the wound 10 has introduced therein two drainage hoses 16 and 18. The drainage hose 16 is connected with the supply line 22, while the drainage hose 18 is connected with the removal line 26. A branching is thus unnecessary.

In the illustrative embodiment according to FIG. 1 the drainage hose 16 forms a hose dead-end, in which on the one hand the active substance can be introduced and out of which on the other hand the active substance can be suctioned out. Thereby during the introduction of the fluid active substance gas bubbles can be trapped in the drainage hose 16, which would interfere with the introduction of the active substance. This difficulty cannot occur in the embodiment according to FIG. 2, since any gas bubbles trapped in the drainage hose 16 would be suctioned out via the drainage hose 18. The embodiment according to FIG. 1 however has the advantage, that only one drainage hose must be introduced under seal under the foil 14.

Figure 3:
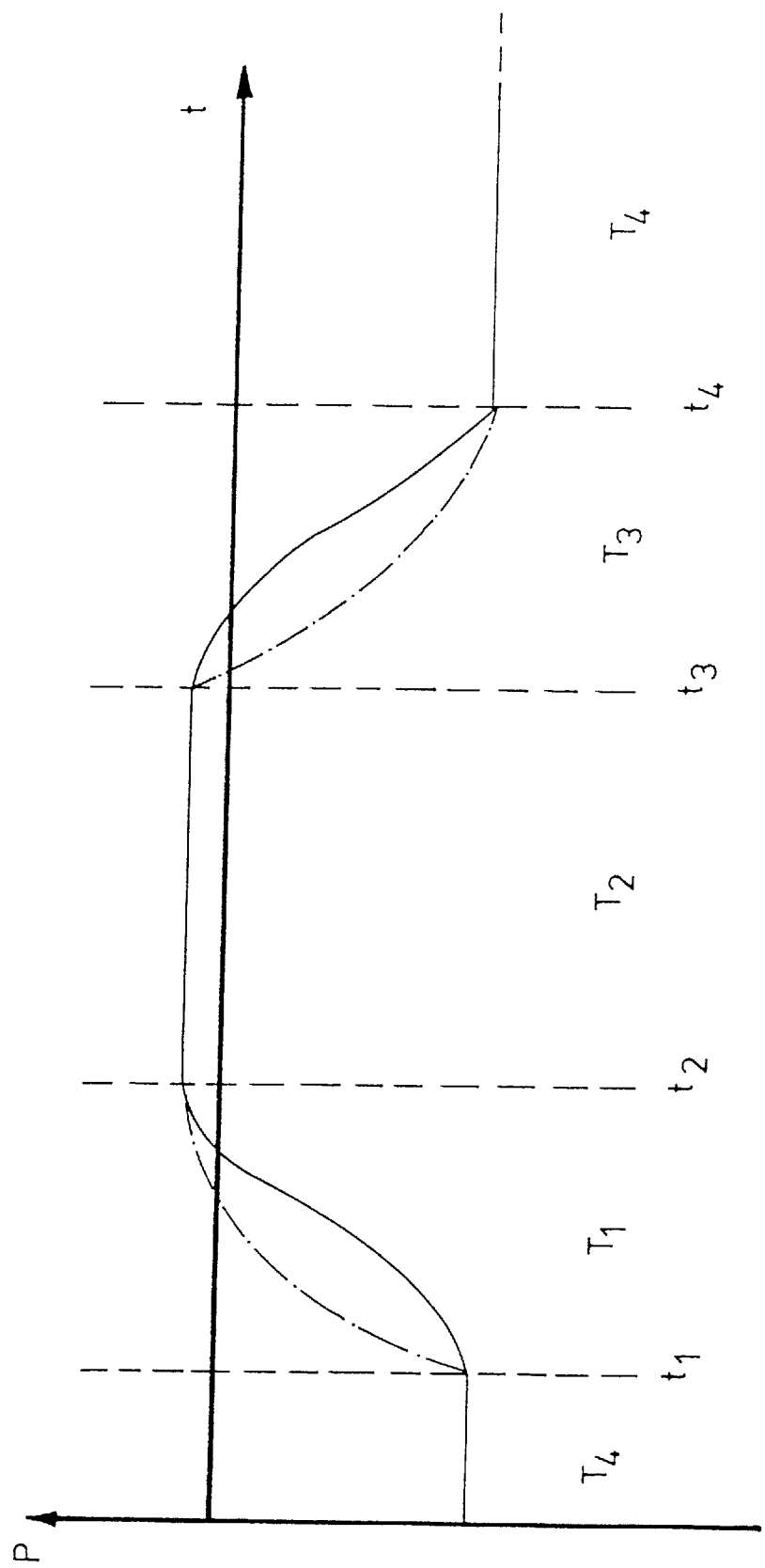

By reference to FIG. 3 the process associated with the device of FIGS. 1 and 2 is further explained.

In FIG. 3 the pressure P existing in the wound 10 under the foil 14 is represented as a function of time t. The actual abscissa axis corresponds herein to the atmospheric pressure. At the time $t_1$ the closure mechanisms 32 and 34 are controlled by the controller 36 to be closed. In the wound there exists a vacuum of approximately 10 to 80 kPa. On the basis of this vacuum the foil 14 is pressed against the wound surface, wherein the elastic padding 12 is compromised. At the time $t_1$ there is now controlled by the controller 36 that the closure mechanism 32 is opened, so that the fluid active substance can flow out of the infusion container 24 via the supply line 22 and the drainage hose 16 into the padding 12. During the inflow time interval $T_1$ the padding 12 suctions itself to fullness with fluid active substance, whereby it expands on the basis of its elastic spring resilience. At the time $t_2$ the padding 12 is suctioned full of fluid active substance, whereby under the foil 14 a certain overpressurization exists, which is preferably determined by the height of the infusion container 24 with respect to the wound 10. In certain cases a pressure controlled pump can be introduced in the supply line 22 controlled by the pressure sensor 38.

The opening of the closure mechanism 32 of the supply line 22 in the introduction time interval $T_1$ is controlled by means of the controller 36 in such a timed manner, that the volumetric flow of the fluid active substance only increases slowly, which in FIG. 3 is shown by the continuous line. A sudden opening of the closure mechanism 32 would result in a very rapid influx of the active substance, as shown in FIG. 3 with a dash-and-period line. This can result in wound pain to the patient, in particular since the fluid active substance as a rule does not correspond to the body temperature of the patient.

During the vacuum phase in certain circumstances the pores of the compromised padding 12 can adhere or stick together. Such an adhesion prevents the influx of the active substance under only gravity, which is determined by the height of the infusion container 24 with respect to the wound 10. Such a possible adhesion of the pores can be rinsed clean thereby that during the opening of the closure mechanism 32 first a certain volume of the fluid active substance is introduced under pressure. For this a suitable volume of the active substance can be introduced by means of a piston syringe via the supply line 22. The piston syringe is therefore preferably connected to the supply line 22, for which for example a three-way cock or valve can be associated with the supply line 22, onto which the piston syringe is connected.

As soon as the padding 12 has suction-filled itself with fluid active substance, the closure mechanism 32 of the supply side 22 is closed at time $t_2$. For a treatment dwell time interval $T_2$ the closure mechanisms 32 and 34 of the supply line 22 and the removal line 26 remain closed, so that the active substance contained in the padding 12 can act upon the surface of the wound 10. The duration of the treatment dwell time interval $T_2$ can be predetermined by the controller 36 and is based upon the type and condition of the wound 10 and according to the type and concentration of the active substance. When the active substance during the time interval $T_2$ has had a sufficient effect or action upon the wound surface, then at time $t_3$ the closure mechanism 34 of the removal line 26 is opened. Thereby via the vacuum existing through the connection line 30 the fluid active substance is suctioned out of the padding 12 and the wound 10 via the drainage hose 16 (in FIG. 1) or as the case may be the drainage hose 18 (in FIG. 2). At the same time the wound fluid or secretion is suctioned out, which has accumulated in the wound in the treatment dwell time interval $T_2$ and which contains decomposition and breakdown products produced through the action of the active substance.

The opening of the closure mechanism 34 is timely so controlled by the controller 36, that the flow-through cross-section of the removal line 26 opens only slowly and the vacuum in the padding 12 and the wound 10 only increases gradually, as this is shown in FIG. 3 through the continuous line. An immediate and complete opening of the closure mechanism 34 would lead to a very rapid pressure drop in the area of the wound which is shown via a dash-and-dot line in FIG. 3, which would be associated with wound pains for the patient.

Should at time $t_4$ the original vacuum again be achieved, which in certain cases can be monitored by the pressure sensor 38, so the fluid active substance can again be completely removed from the wound 10 and the padding 12. The vacuum is then maintained for a vacuum time interval $T_4$. Thereby as a rule the closure mechanism 34 remains open, so that the vacuum is continuously maintained by the vacuum source 30, and the produced wound secretion is continuously suctioned off into the receptacle retainer 28. It is also possible, that the closure mechanism 34 is closed or temporarily closed and only opened for short period of times when the vacuum monitored by pressure sensor 38 must be regenerated.

In the case that the next treatment of the wound 10 is to be accomplished with a fluid active substance, then at time $t_1$ the closure mechanism 34 is closed and then closure mechanism 32 of supply line 24 is again opened so that the described cycle again starts from the beginning.

In place of the shown electromagnetic, pneumatic or hydraulic operated hose clamps 32 and 34 shown in FIGS. 1 and 2 the closure mechanisms for the supply line 22 and the removal line 26 can be constructed as multi-way valves. Appropriate examples are shown in FIGS. 4 through 8. The construction of the closure device as a multi-way valve results in a simple construction and a reliable switching of the closure device. In particular there results a simplified control of the closure device, when the multi-way valve is controlled by means of a electrical step motor, which in a simple manner can be achieved by the respective driving of the plug or cock via the respective step motor. The re-positioning of the multi-way valve via a step motor makes possible a simple electronic control. This control can be programmed in a simple manner and with great flexibility, in order to achieve an adaptation to the desired treatment cycle. The control and the treatment cycle can in this manner be programmed individually for each patient and each indication. Also the opening and closing of the multi-way valve can be precisely and flexibly temporally controlled electrically by the step motor in order to realize the pressure sequence shown in FIG. 3.

In the FIGS. 4 through 8 there are shown respectively only the closure mechanisms of the device. Otherwise the device corresponds to the examples of FIGS. 1 and 2.

In the illustrative embodiment in FIG. 4 only one drainage hose 16 is provided. The supply line 22 and the removal line 26 are alternatively communicating with the drainage hose 16 via a three-way cock or valve 38. By means of the electronic control 36 a here not shown step motor is programmably controlled, which operates the three-way valve 38. In the position "a" the supply line 22 is connected to the drainage hose 16 via a three-way valve 38, so that the active substance can be introduced into the porous padding 12. Subsequently the three-way valve 38 is repositioned to position "b", in which the drainage hose 16 is blocked, in order that the introduced active substance can work on the wound. For suctioning off the three-way valve 38 is rotated to position "c", in which the drainage hose 16 is connected to the drainage line 26.

The illustrative embodiment of FIG. 5 shows the device with a drainage hose 16 for the supply and a drainage hose 18 for the suctioning. Both in the supply line 22 as well also in the removal line 26 there is interposed respectively a two-way valve 40 or as the case may be 42, so that the functionality results, which is described in the illustrative embodiment according to FIG. 2. In the position "a" the two-way valve 40 is open and the two-way valve 42 closed, so that the supply line 22 is connected to the drainage hose 16, while the drainage hose 18 is blocked. In this position "a" the fluid active substance is introduced via the drainage hose 16 into the padding 12.

Subsequently the two-way valve 40 is closed, so that the position "b" is assumed. Both the supply line 22 as well also the removal line 26 are blocked, so that the active substance received by the padding 12 can act. After ending the active dwell phase, the two-way valve 42 is opened, corresponding to position "c", so that now the active substance and any secretion which may be present can be suctioned off via the drainage hose 18 and the removal line 26. After a more-or-less lengthy vacuum interval it is switched back to position "a", in order to reintroduce a treatment substance.

The embodiment according to FIG. 6 corresponds functionally to the illustrative embodiment according to FIG. 5. Essentially in place of the two two-way valves 40 and 42 one four-way valve 44 is provided. The four-way valve 44 connects in position "a" the supply line 22 with the drainage hose 16, blocks in position "b" both the supply line 22 as well also the removal line 26, and connects in position "c" the removal line 26 with the drainage hose 18.

In the until now described embodiments there is respectively provided only one supply line 22, so that only one infusion container 24 can be connected. Should various active substances be supplied, then the infusion container 24 connected with the supply line 22 must be changed out. Likewise the infusion container 24 must be removed and be traded out with a piston syringe, when the padding 12 in the case of adhesion of the pores should be rinsed clean. These disadvantages can be overcome by the illustrative embodiment of FIGS. 7 and 8.

The illustrative embodiment according to FIG. 7 corresponds with the illustrative embodiments of FIG. 1 insofar, that only one drainage hose 16 is provided for the supply and the removal. The drainage hose 16 is connected via two in-line associated three-way valves 46 and 48. The first three-way valve 46 selectively connects a first supply line 22.1 or a removal line 26 to the connecting line to the second three-way valve 48. The second three-way valve 48 selectively connects this connection line or a second supply line 22.2 to the drainage hose 16. In the position "a" the first three-way valve 48 connects the first supply line 22.1 with the connection line and the second three-way valve 48 of this connection line with the drainage hose 16. A first active substance can be introduced via the first supply line 22.1. The second supply line 22.2 and the removal line 26 are blocked. In position "b" the first three-way valve 46 blocks any connections, while the second three-way valve 48 connects the second supply line 22.2 with the drainage hose 16. In this position a second active substance can be introduced via the supply line 22.2. In the position "c" both three-way valves 46 and 48 block all supply lines, so that the introduced active substances can act over a controllable time interval. Subsequently in position "d" the drainage hose 16 is connected via the second three-way valve 48 with the connection line, while the first three-way valve 46 connects the connection line with the removal line 26. At this time the active substance and any wound secretion can be suctioned from padding 12 via the drainage hose 16 and the removal line 26.

The embodiment according to FIG. 7 was also suitable therefore, to rinse clean the padding 12 at the beginning of the introduction phase. In this case a piston syringe is connected to the supply line 22.1, while on the supply line 22.2 the infusion container 24 is connected. First in the position "a" the adhered padding 12 is rinsed clean by means of the piston syringe, in order then in the position "b" the active substance is supplied from the infusion container 22 by gravity via the second supply line 22.2. The rinsing clean by means of a piston syringe can thus be carried out, without requiring any change in the connection of the connections.

In this embodiment it is also possible that the infusion container 24 connected to the second supply line 22.2 be used only as a supply container for the fluid active substance and to apply this exclusively by means of the syringe connected in the first supply line 22.1. For this the first three-way valve 46 is brought into the position of FIG. 7a, while the second three-way valve 48 in comparison to this position is so rotated or repositioned, that it connects the second supply line 22.2 with the connection line to the first three-way valve 46. Now the fluid active substance can be conveyed out of the infusion container 24 connected via the first three-way valve 46 into the piston syringe connected to the first supply line 22.1, in order to fill this. As soon as the piston syringe is filled, the second three-way valve 48 is brought into the position of FIG. 7a, so that the fluid active substance can now be applied by means the piston syringe.

FIG. 8 shows an embodiment, which again corresponds to the principle of the main embodiment of FIG. 2, in which one drainage hose 16 is provided for the supply and one drainage hose 18 for the removal. The introduction can however be accomplished via two supply lines 22.1 and 22.2. There exists herewith also the possibility to supply two different active substances via the supply lines 22.1 and 22.2 or via one of the supply lines to supply the active substance via the syringe and via the second supply line to supply the active substance from an infusion container. The drainage hose 16 is connectable with the two supply lines 22.1 and 22.2 via a three-way valve 50, while the drainage hose 18 is connected to the removal line 26 via a two-way valve 52. In the position "a" the first supply line 22.1 is connected with the drainage hose 16, in order to supply a first active substance or in order to rinse clean the padding 12. The two-way valve 52 blocks the second drainage hose 18. In the position "b" a second active substance is supplied via the second supply line 22.2. In the position "c" the three-way valve 50 as well also as the two-way valve 52 are blocked for the action of the active substance. In the position "d" the three-way valve 50 blocks all connections, while the two-way valve 52 connects the drainage hose 18 with the removal line 26 in order to suction off the active substance.

Here also an infusion container 24 can be connected to the attachment 22.2, which is employed only as supply container for the fluid active substance, while this fluid active substance is applied via a syringe connected to the supply line 22.1. In a position rotated about 180° to that of position "b" the three-way valve 50 connects thereby the supply infusion container 54 connected to the supply line 22.2 with the piston syringe connected to the supply line 22.1, in order to fill this.

What is claimed is:

1. A process for application of active substances to a wound surface of a wound having a rim, said process comprising:

applying a padding of a porous material upon the wound surface;

providing a cover over the wound surface and the padding, and sealingly securing said cover onto the skin surface about the rim of the wound;

introducing at least one fluid active substance via at least one supply line into the padding; and removing said at least one fluid active substance by suctioning out of the padding, wherein the introducing and the suctioning out of the active substance is timely controlling in such a manner, that the introduction and the suctioning off are conducted in separate, not overlapping time intervals (respectively $T_1$ and $T_3$) and that a dwell time interval ($T_2$) is provided between the introduction of and the suctioning off of the active substance.

2. A process according to claim 1, wherein subsequent to the suctioning off ($T_3$) of the active substance and before the next introduction ($T_1$) a vacuum time interval ($T_4$) is provided, in which a vacuum is maintained under said cover.

3. A process according to claim 1, wherein the introduction of the active substance occurs under a temporally controlled slow increase of the volumetric flow of the active substance.

4. A process according to claim 1, wherein at the beginning of the introduction of the active substance a predetermined volume of the active substance is introduced under sufficient pressure to cause said active substance to rinse through the porous padding.

5. A process according to claim 1, wherein said porous material is an elastic compressible porous material.

6. A process for application of active substances to a wound surface of a wound having a rim, said process comprising:

applying a padding of a porous material upon the wound surface;

providing a cover over the wound surface and the padding, and sealingly securing said cover onto the skin surface about the rim of the wound;

introducing at least one fluid active substance via at least one supply line into the padding; and removing said at least one fluid active substance by suctioning out of the padding, wherein the introducing and the suctioning out of the active substance is timely controlling in such a manner, that the introduction and the suctioning off are conducted in separate, not overlapping time intervals (respectively $T_1$ and $T_3$) and that a dwell time interval ($T_2$) is provided between the introduction of and the suctioning off of the active substance, wherein said suctioning off occurs with a temporally controlled slowly increasing vacuum.

7. A process for application of active substances to a wound surface of a wound having a rim, said process comprising:

applying a padding of an elastic compressible porous material upon the wound surface;

providing a cover over the wound surface and the padding, and sealingly securing said cover onto the skin surface about the rim of the wound;

introducing at least one fluid active substance via at least one supply line into the padding; and removing said at least - one fluid active substance by suctioning out of the padding, wherein the introducing and the suctioning out of the active substance is timely controlling in such a manner, that the introduction and the suctioning off are conducted in separate, not overlapping time intervals (respectively $T_1$ and $T_3$) and that a dwell time interval ($T_2$) is provided between the introduction of and the suctioning off of the active substance, and wherein subsequent to the suctioning off ($T_3$) of the active substance and before the next introduction ($T_1$) a vacuum time interval ($T_4$) is provided, in which a vacuum is maintained under said cover.

8. A process according to claim 8, wherein said porous material is an elastic compressible porous material, wherein a closure mechanism is provided in said supply line, wherein removal occurs via a removal line, wherein a closure mechanism is provided in said removal line, and wherein said vacuum during said vacuum time interval ($T_4$) is maintained constant by closing said closure mechanisms after establishment of a vacuum under said cover.

* * * * *